United States Patent
Bo et al.

(10) Patent No.: US 11,639,336 B2
(45) Date of Patent: May 2, 2023

(54) PREPARATION METHOD FOR S-INDOXACARB

(71) Applicant: SHANDONG JINGBO AGROCHEMICALS TECHNOLOGY CO., LTD., Shandong (CN)

(72) Inventors: Leifang Bo, Binzhou (CN); Daoquan Cheng, Binzhou (CN); Jiancheng Liu, Binzhou (CN); Peiliang Feng, Binzhou (CN); Huamin Liu, Binzhou (CN); Zhongyang Wang, Binzhou (CN)

(73) Assignee: SHANDONG JINGBO AGROCHEMICALS TECHNOLOGY CO., LTD., Binzhou (CN)

( * ) Notice: Subject to any disclaimer, the term of this patent is extended or adjusted under 35 U.S.C. 154(b) by 365 days.

(21) Appl. No.: 16/954,081

(22) PCT Filed: Apr. 25, 2019

(86) PCT No.: PCT/CN2019/084224
§ 371 (c)(1),
(2) Date: Jun. 15, 2020

(87) PCT Pub. No.: WO2019/233209
PCT Pub. Date: Dec. 12, 2019

(65) Prior Publication Data
US 2021/0171476 A1    Jun. 10, 2021

(30) Foreign Application Priority Data
Jun. 8, 2018 (CN) .................... 201810591874.7

(51) Int. Cl.
| | | |
|---|---|---|
| *C07D 273/04* | (2006.01) | |
| *B01J 31/22* | (2006.01) | |
| *B01J 31/40* | (2006.01) | |
| *C07B 53/00* | (2006.01) | |
| *C08G 12/06* | (2006.01) | |
| *C07C 67/31* | (2006.01) | |

(52) U.S. Cl.
CPC ........ *C07D 273/04* (2013.01); *B01J 31/2217* (2013.01); *B01J 31/4015* (2013.01); *C07B 53/00* (2013.01); *C07C 67/31* (2013.01); *C08G 12/06* (2013.01); *C07B 2200/07* (2013.01); *C07C 2602/08* (2017.05)

(58) Field of Classification Search
CPC . C07D 273/04; B01J 31/2217; B01J 31/4015; B01J 31/1691; B01J 31/2243; B01J 2531/0216; B01J 2531/0252; B01J 2531/04; B01J 2531/48; C07B 53/00; C07B 2200/07; C07C 67/31; C07C 2602/08; C08G 12/06
See application file for complete search history.

(56) References Cited

FOREIGN PATENT DOCUMENTS

| CN | 1630555 A | 6/2005 | |
|---|---|---|---|
| CN | 101062903 A | 10/2007 | |
| CN | 106397351 A | 2/2017 | |
| WO | WO-03002255 A1 * | 1/2003 | .......... B01J 31/2234 |

OTHER PUBLICATIONS

Zheng; "Study on synthesis process of novel chiral insecticide indoxacarb and its polymorphism;" Master Dissertation; 2014; Institute of Pesticide & Environmental Toxicology, College of Agriculture and Biotechnology, Zhejiang University, Hangzhou, China.
Jul. 26, 2019 Search Report issued in International Patent Application No. PCT/CN2019/084224.

* cited by examiner

*Primary Examiner* — John M Mauro
(74) *Attorney, Agent, or Firm* — Oliff PLC

(57) ABSTRACT

A catalyst and a method for preparing S-indoxacarb using the catalyst. The catalyst is prepared using 3-tert-butyl-5-(chloromethyl)salicylaldehyde and cyclohexanediamine as raw materials, where an original quinine catalyst such as cinchonine is replaced with the catalyst for application in the asymmetric synthesis of tert-butyl hydroperoxide and 5-chloro-2-methoxycarbonyl-1-indanone ester, greatly improving selection in the asymmetric synthesis process, with the S-enantiomer content increasing from 75% to over 98%, achieving the recycling of a high-efficiency chiral catalyst, and greatly reducing production costs. The synthesis process of the catalyst is simple and is favorable for industrialization, and lays good foundations for the production of high-quality indoxacarb.

8 Claims, No Drawings

PREPARATION METHOD FOR S-INDOXACARB

INCORPORATION BY REFERENCE

The preparation method of the S-indoxacarb is described in the paper "Study on Synthesis Process of Novel Chiral Insecticide Indoxacarb and Its Polymorphism," with which a master's degree was awarded by Zhejiang University in 2014, which is fully incorporated herein in its entirely by reference.

TECHNICAL FIELD

The invention relates to a field of chemical synthesis, and specifically releases a preparation method for S-indoxacarb.

BACKGROUND TECHNOLOGY

Indoxacarb is a new, highly effective and low toxic oxadiazine pesticide developed by DuPont Company of the United States. It has double effects of contact killing and stomach toxicity, and effectively solves resistant pests. It has no cross-resistance with other pesticides such as pyrethrin, organophosphorus and carbamate, and can well solve the problems of rice leaf-roller, *Chilo suppressalis* and resistant diamondback moth, which are difficult to prevent in the current market. In addition, indoxacarb has a very broad insecticidal spectrum: One pesticide can control multiple pests. It has a good inhibitory effect on blind stink bugs while controlling spodoptera pests, so it is a good comprehensive management tool, which can solve the problem of residue and environmental pollution after mixed use of multiple pesticides. Indoxacarb, due to its unique mechanism of action and broad market prospects, was registered for selling on the markets in many countries such as the United States, France, China and other countries in 2001 as a "Risk Reduction Product". It is the latest variety of green pesticide at present, and also a substitute for high toxicity and high residue pesticide varieties widely demonstrated and popularized by China's Ministry of Agriculture. In 2008, its global sales reached more than 200 million US dollars.

The application date of the patent application of the product in China is Dec. 21, 1991, and expired on Dec. 21, 2011. With the end of indoxacarb patent period, many domestic enterprises began to research the synthesis process of products and produce them, but the original pesticide of indoxacarb that they achieved through synthesis is a mixture of S and R (S:R=3:1), in which the R-enantiomer in the original pesticide has no efficacy but causes environmental pollution and high cost of medicine. Therefore, the development of a synthetic method of the S-indoxacarb has become a hot topic at home and abroad. At present, there are two main catalysts used in the synthesis of indoxacarb:

First, using quinine catalysts such as cinchonine, but the efficiency of these catalysts is low, and the content of the S-enantiomer of the synthetic S-indoxacarb is about 70%.

Second, using metal complex catalysts. In 2007, DuPont reported a metal zirconium catalyst, but this kind of catalyst cannot be recycled, the production cost is high, and the content of the S-enantiomer of the obtained S-indoxacarb is about 90%.

Therefore, how to overcome the defects of the catalyst and the synthesis method in the synthesis process of the S-enantiomer of S-indoxacarb has become one of the problems urgently to be solved in the art.

Content of Invention

The purpose of the invention is to overcome the disadvantages of the prior art, provide a brand-new catalyst and a method for preparing S-indoxacarb using the catalyst. The catalyst is prepared with 3-tert-butyl-5-(chloromethyl)salicylaldehyde and cyclohexanediamine as raw materials, and replaces the original quinine catalysts such as cinchonine with the catalyst, which is applied in the asymmetric synthesis of tert-butyl hydroperoxide and 5-chloro-2-methoxycarbonyl-1-indanone ester, the selectivity in the asymmetric synthesis process is greatly improved, the S-enantiomer content is increased from 75% to over 98%, and the recycling of high-efficiency chiral catalyst is realized, and the production cost is greatly reduced. The synthesis process of the catalyst is simple, which is favorable for industrialization and lays a good foundation for the production of high-quality indoxacarb.

The technical scheme of the invention is as follows:

The inventor first provided a brand-new chiral catalyst containing zirconium, and the preparation reaction equation is as follows:

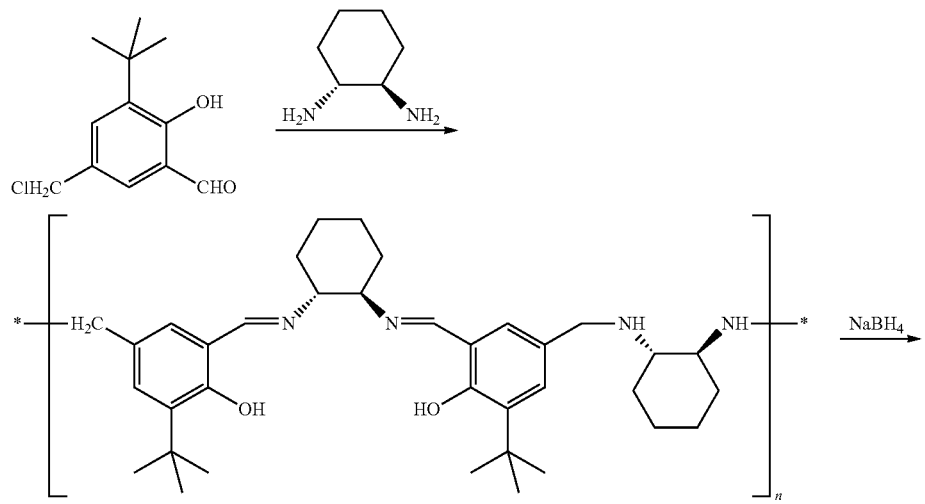

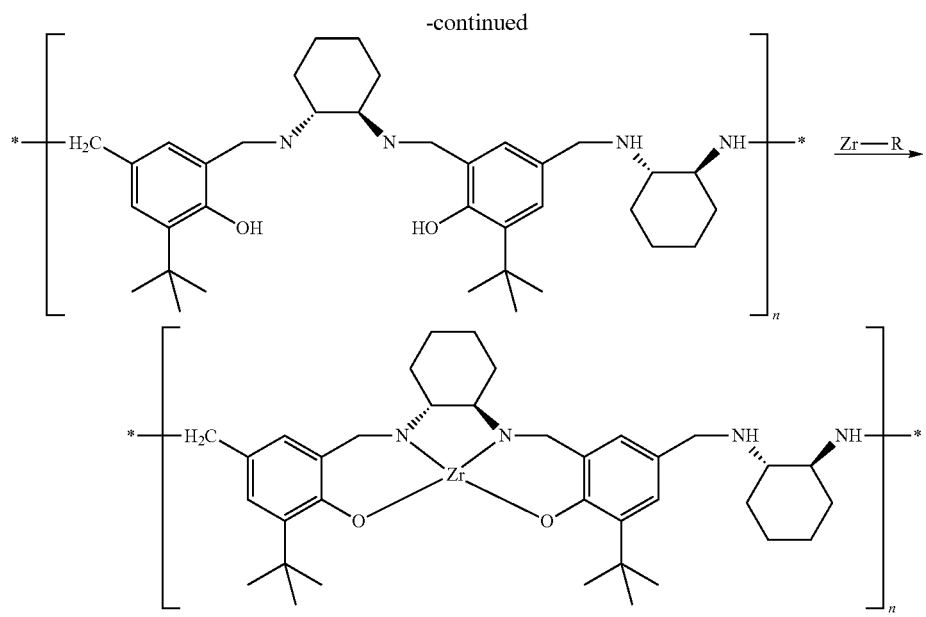

The specific steps are as follows:

(1) Adding 3-tert-butyl-5-(chloromethyl)salicylaldehyde and solvent to a reaction flask at 20-30° C., then adding cyclohexanediamine into the system, and controlling a drop rate to 0.1 mL/min.

Wherein, the cyclohexanediamine is chiral cyclohexanediamine. A mole ratio of 3-tert-butyl-5-(chloromethyl)salicylaldehyde to cyclohexanediamine is 1:1-1.5. The amount of the solvent is 4-6 times of the mass of 3-tert-butyl-5-(chloromethyl)salicylaldehyde.

The above said solvent in step(1) is selected from methanol, ethanol, dichloromethane and dichloroethane.

Methanol is preferred.

(2) After dropping, raising the temperature to 40-80° C. for reflux reaction. After the reflux reaction, lower the temperature to 0-20° C., and a ligand polymer is obtained after filtration, then weighing the ligand polymer after drying.

(3) Putting the ligand polymer obtained in the previous step and the solvent of twice the mass of the ligand polymer into a reaction flask, then putting the reducing agent into the reaction flask, raising the temperature to 80-140° C., and carrying out the reflux reaction for 4-6 hours.

The above said solvent in step(3) is selected from toluene, xylene, dichloroethane, n-hexane and tert butanol.

Toluene is preferred.

The reducing agent is selected from sodium borohydride, potassium borohydride and lithium aluminum hydride, and a mole ratio of the reducing agent to 3-tert-butyl-5-(chloromethyl)salicylaldehyde is 1-1.2:1.

(4) Adding a zirconium compound to the above system, raising the temperature to 80-100° C. after being fully swelling. After heat preservation reaction for 2-4 hours, the polymerization catalyst solution is obtained.

The above said zirconium compound is selected from zirconium hydroxide, zirconyl chloride octahydrate, zirconium dioxide, zirconium tetrachloride, zirconium(IV) acetylacetonate, zirconium trifluoroacetylacetonate, n-propyl zirconate, zirconium(IV) tert-butoxide, zirconium(IV) hydrogenphosphate and zirconium(IV) bromide.

Zirconium(IV) acetylacetonate is preferred.

And a mole ratio of the zirconium compound to 3-tert-butyl-5-(chloromethyl)salicylaldehyde is 1:1-2.

In the above preparation process:

Firstly, putting 3-tert-butyl-5-(chloromethyl)salicylaldehyde and methanol into the reaction flask, and then adding cyclohexanediamine into the system. Cyclohexanediamine plays a role of bridge connection in the reaction process so that different 3-tert-butyl-5-(chloromethyl)salicylaldehyde are connected into the complex monomer. Make the generated complex monomer uniform and controllable by controlling the drop acceleration of cyclohexanediamine; then raising the temperature to make different monomers polymerize. Prolonged reflux makes the monomer fully polymerized. After all polymers are formed, due to the large molecular weight of the polymers and its poor solubility in the solvent, the polymers are gradually separated out in the system. The polymer ligands are obtained by filtration after cooling.

Secondly, adding toluene and the above-mentioned polymer ligands to the reaction flask, then adding a reducing agent to make C═N undergo hydrogenation reduction, so that N provides electron pairs to for coordination, and then adding a metal zirconium compound to the system. Because of the poor solubility of the polymer in toluene, it shall be fully swelled and soaked. The metal penetrates into the polymer ligand through a high-temperature reaction at elevated temperature to undergo coordination reaction to generate a complex catalyst for polymerizing organic ligands. Since the polymer ligand is insoluble in toluene, the generated complex catalyst is suspended in toluene solvent. The subsequent preparation of S-indoxacarb can be directly carried out by taking it as a reaction system, specifically as follows:

After obtaining the above-mentioned catalyst, the inventors applied it to the preparation process of S-indoxacarb. The preparation process of the S-indoxacarb is as follows: (for this process, please refer to the synthetic route published in the paper "*study on synthesis process of novel chiral*

*insecticide indoxacarb and its polymorphism*", with which a master's degree was awarded by Zhejiang University in 2014).

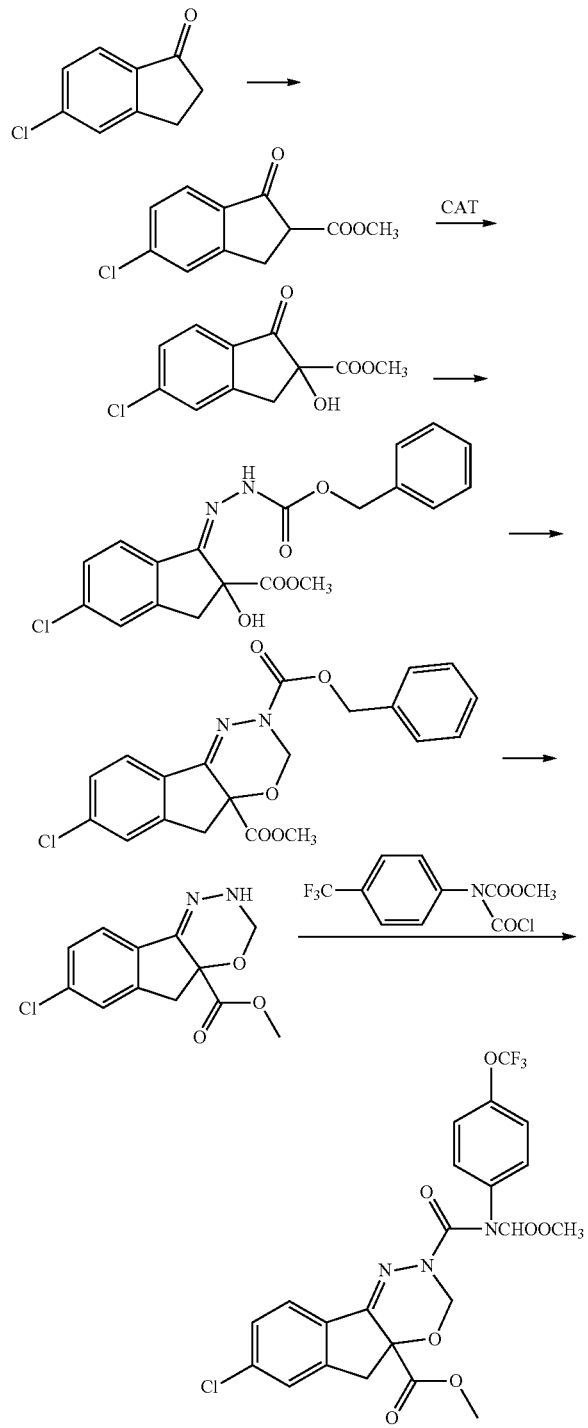

The above reaction process is similar to the conventional technique, but the process of converting 5-chloro-2-methoxycarbonyl-1-indanone ester to 5-chloro-2-methoxycarbonyl-2-hydroxy-1-indanone used the above said catalyst. The specific reaction process is as follows:

The above reactions are asymmetric synthesis reactions. The specific steps are as follows:

Adding tert-butyl hydroperoxide and 5-chloro-2-methoxycarbonyl-1-indanone ester to the polymerization catalyst solution obtained by the above method to carry out asymmetric synthesis, wherein the mole ratio of 5-chloro-2-methoxycarbonyl-1-indanone ester:tert-butyl hydroperoxide:catalyst is 1:1.2-1.5:0.05-0.1. Raising the temperature to 60-120° C. for reflux reaction for 4 hours. Filtering the obtained mixture to recover polymer catalyst. The key intermediate 5-chloro-2-methoxycarbonyl-2-hydroxy-1-indanone can be obtained by vacuum distillation of the filtrate. Putting the recovered catalyst into toluene solvent to form suspension to continue to participate in the asymmetric synthesis reaction.

After obtaining the above-mentioned 5-chloro-2-methoxycarbonyl-2-hydroxy-1-indanone, it can react with carbobenzoxyhydrazide and diethoxymethane according to the above-mentioned conventional synthesis route. And finally, with hydrogenating deprotection, synthesize S-indoxacarb with 4-trifluoromethoxy phenyl carbamate.

The finally obtained S-indoxacarb has been tested and it is found that the content of S-indoxacarb is more than 98%, which is much higher than the content of about 70% using quinine catalysts such as cinchonine, and also significantly higher than 90% of S-indoxacarb prepared through zirconium catalyst reported by DuPont Company.

Meanwhile, using the above said catalyst and method provided by this invention, the catalyst can be recycled, greatly reducing the production cost. The synthesis process of the catalyst is simple and is favorable for industrialization, and lays good foundations for the production of high-quality indoxacarb.

In conclusion, original pesticide of S-indoxacarb with the content of the S-enantiomer ≥98% can be prepared by using the catalyst provided by this invention. Using the high-efficiency chiral catalyst instead of an original quinine catalyst such as cinchonine greatly improves the selectivity in the asymmetric synthesis process, and increases the content of the S-enantiomer from 75% to more than 98%. Among them, the preparation of the chiral catalyst introduced metal zirconium compounds, which greatly improved the reaction rate of asymmetric reactions. The reaction time has been shortened from 24 hours to 4 hours. At the same time, it is equipped with chiral diamine ligands and the selectivity in the asymmetric synthesis process is increased. The introduction of organic polymer ligands realizes the recycling of the high-efficiency chiral catalyst, which greatly reduces the production cost. The synthesis process of this catalyst is simple, which is favorable for industrialization and lays good foundations for the production of high-quality indoxacarb.

SPECIFIC EMBODIMENTS

Embodiment 1: A Chiral Catalyst Containing Zirconium and a Preparation Method for S-Indoxacarb by Using this Catalyst The preparation method is as follows:

(1) Add 22.65 g (0.1 mol) of 3-tert-butyl-5-(chloromethyl) salicylaldehyde to a 100 ml clean and anhydrous reaction flask, then add 50 ml of methanol, and then weigh 11.4 g (0.1 mol) of cyclohexanediamine and add it slowly at 20-25° C.

(2) After adding, raise the temperature to 65-70° C. for reflux reaction. After the reaction, lower the temperature to 10° C., and a ligand polymer is obtained after filtration, then weigh the ligand polymer after drying.

(3) Put the ligand polymer obtained in step (2) into a 2000 ml clean and anhydrous reaction flask, then add 50 ml toluene and 3.78 g (0.1 mol) sodium borohydride. Raise the temperature for the reflux reaction.

(4) Add 24.35 g (0.05 mol) of zirconium(IV) acetylacetonate to the above said reaction system. Raise the temperature to 80° C. after being fully soaked. The toluene solution of the polymerization catalyst is obtained through heat preservation reaction.

The method for preparing the S-indoxacarb by using the above said catalyst can adopt the conventional synthesis route disclosed in the paper "study on synthesis process of novel chiral insecticide indoxacarb and its polymorphism", with which a master's degree was awarded by Zhejiang University in 2014. Wherein:

(5) Add 225 g of tert-butyl hydroperoxide, 449 g of 5-chloro-2-methoxycarbonyl-1-indanone ester and 1000 mL of toluene to the catalyst toluene solution obtained in the above step (4) to carry out asymmetric synthesis reaction. Raise the temperature to 110° C. for the reflux reaction for 4 hours; after completion of the reaction, filter it to get the metal polymer catalyst. The key intermediate 5-chloro-2-methoxycarbonyl-2-hydroxy-1-indanone can be obtained by vacuum distillation of the filtrate. Put the recovered catalyst into 50 ml toluene solvent to form suspension to continue to participate in the asymmetric synthesis reaction.

(6) The key intermediate 5-chloro-2-methoxycarbonyl-2-hydroxy-1-indanone which is obtained in the above step (5) reacts with carbobenzoxyhydrazide and diethoxymethane according to the conventional synthesis route shown in the description. And finally, with hydrogenating deprotection, synthesize S-indoxacarb with 4-trifluoromethoxy phenyl carbamate. The testing result of the content of S-enantiomer is 98.6%.

Embodiment 2: A Chiral Catalyst Containing Zirconium and a Preparation Method for S-Indoxacarb by Using this Catalyst The preparation method is as follows:

(1) Add 22.65 g (0.1 mol) of 3-tert-butyl-5-(chloromethyl) salicylaldehyde to a 100 ml clean and anhydrous reaction flask, then add 50 ml of methanol, and then weigh 17.1 g (0.15 mol) of cyclohexanediamine and add it slowly at 20-25° C.

(2) After adding, raise the temperature to 65-70° C. for reflux reaction. After the reaction, lower the temperature to 10° C., and a ligand polymer is obtained after filtration, then weigh the ligand polymer after drying.

(3) Put the ligand polymer obtained in step (2) into a 2000 ml clean and anhydrous reaction flask, then add 50 ml toluene and 5.4 g (0.1 mol) potassium borohydride. Raise the temperature for the reflux reaction.

(4) Add 24.35 g (0.05 mol) of zirconium(IV) acetylacetonate to the above said reaction system. Raise the temperature to 80° C. after being fully swelling. The toluene solution of the polymerization catalyst is obtained through heat preservation reaction.

The method for preparing the S-indoxacarb by using the above said catalyst can adopt the conventional synthesis route disclosed in the paper "study on synthesis process of novel chiral insecticide indoxacarb and its polymorphism", with which a master's degree was awarded by Zhejiang University in 2014. Wherein:

(5) Add 113 g of tert-butyl hydroperoxide, 224 g of 5-chloro-2-methoxycarbonyl-1-indanone ester and 1200 mL of toluene to the catalyst toluene solution obtained in the above step (4) to carry out asymmetric synthesis reaction. Raise the temperature to 110° C. for the reflux reaction for 4 hours; after completion of the reaction, filter it to get the metal polymer catalyst. The key intermediate 5-chloro-2-methoxycarbonyl-2-hydroxy-1-indanone can be obtained by vacuum distillation of the filtrate. Put the recovered catalyst into 50 ml toluene solvent to form suspension to continue to participate in the asymmetric synthesis reaction.

(6) The key intermediate 5-chloro-2-methoxycarbonyl-2-hydroxy-1-indanone which is obtained in the above step (5) reacts with carbobenzoxyhydrazide and diethoxymethane according to the conventional synthesis route shown in the description. And finally, with hydrogenating deprotection, synthesize S-indoxacarb with 4-trifluoromethoxy phenyl carbamate. The testing result of the content of S-enantiomer is 98.9%.

Embodiment 3: Recycling and Utilization of the Metal Polymer Catalyst

Add the catalyst recovered from filtration in Embodiment 2 to toluene; then add 113 g of tert-butyl hydroperoxide, 224 g of 5-chloro-2-methoxycarbonyl-1-indanone ester and 1200 mL of toluene to carry out asymmetric synthesis reaction. Raise the temperature to 110° C. for the reflux reaction for 4 hours; after completion of the reaction, filter it to get the metal polymer catalyst. The key intermediate 5-chloro-2-methoxycarbonyl-2-hydroxy-1-indanone can be obtained by vacuum distillation of the filtrate. Put the recovered catalyst into 50 ml toluene solvent to form suspension to continue to participate in the asymmetric synthesis reaction; the obtained intermediate is prepared according to the conventional prior art to obtain S-indoxacarb.

The results of the correlative experiments such as reuse times, reaction yield and the content of S-enantiomer are as follows:

| Serial number | Yield (%) | The content of S-enantiomer (%) | Remarks |
| --- | --- | --- | --- |
| 1 | 58.1 | 98.9 | the first time for reuse |
| 2 | 57.9 | 98.8 | the second time for reuse |
| 3 | 57.8 | 98.7 | the third time for reuse |
| 4 | 57.7 | 98.5 | the fourth time for reuse |
| 5 | 57.5 | 98.2 | the fifth time for reuse |
| 6 | 57.4 | 97.8 | the sixth time for reuse |
| 7 | 57.3 | 97.3 | the seventh time for reuse |
| 8 | 57.1 | 96.9 | the eighth time for reuse |
| 9 | 57 | 96.4 | the ninth time for reuse |
| 10 | 56.6 | 96 | the tenth time for reuse |

It can be seen that the catalyst structure provided by this invention is stable, and is not easy to be lost during the reaction. The small experiments verify that the content of the S-enantiomer of the indoxacarb obtained after reusing ten times is still higher than the production level of DuPont (the content of the S-enantiomer: 90%). Cost accounting according to ten times of the catalyst reuse, the cost of using the catalyst is reduced more than RMB 30,000 compared with that of DuPont, which has greater economic and environmental benefits.

In conclusion, it can be seen that the catalyst provided by this invention improves the selectivity during asymmetric synthesis, and the S-enantiomer content is increased from 75% to more than 98%. Among them, the preparation of the chiral catalyst introduced metal zirconium compounds, which greatly improved the reaction rate of asymmetric reactions. The reaction time has been shortened from 24 hours to 4 hours. At the same time, it is equipped with chiral diamine ligands and the selectivity in the asymmetric synthesis process is increased.

The invention claimed is:
1. A preparation method for S-indoxacarb, wherein a synthetic reaction is catalyzed by a chiral catalyst containing zirconium, a method of producing the chiral catalyst containing zirconium, comprising the steps of:
step 1
  (a) add 3-tert-butyl-5-(chloromethyl)salicylaldehyde and solvent to a reaction flask at 20-30° C.;
  (b) add chiral cyclohexanediamine to the flask dropwise at a drop rate of 0.1 mL/min;
  after addition of chiral cyclohexanediamine is complete,
step 2
  (a) raise the temperature to 40-80° C.;
  (b) allow the reaction to occur under reflux conditions; then
  (c) lower the temperature to 0-20° C.;
  (d) obtain the resultant ligand polymer by filtration; then
  (e) dry the obtained polymer; and
  (f) weigh the dried polymer;
step 3
  (a) add the dried ligand polymer and a solvent of twice the mass of the polymer to a reaction flask;
  (b) add a reducing agent to the reaction flask;
  (c) raise the temperature to 80-140° C.; and
  (d) reflux for 4-6 hours;
step 4
  (a) add a zirconium compound to the system in step 3, after the system reaches swelling equilibrium, wherein the zirconium compound is selected from the group consisting of zirconium hydroxide, zirconyl chloride octahydrate, zirconium dioxide, zirconium tetrachloride, zirconium(IV) acetylacetonate, zirconium trifluoroacetylacetonate, n-propyl zirconate, zirconium(IV) tert-butoxide, zirconium(IV) hydrogenphosphate and zirconium(IV) bromide;
  (b) raise the temperature to 80-100° C.;
  (c) react at the temperature of 80-100° C. for 2-4 hours, then
  (d) obtain a polymerization catalyst solution;
wherein a reaction equation is as follows:

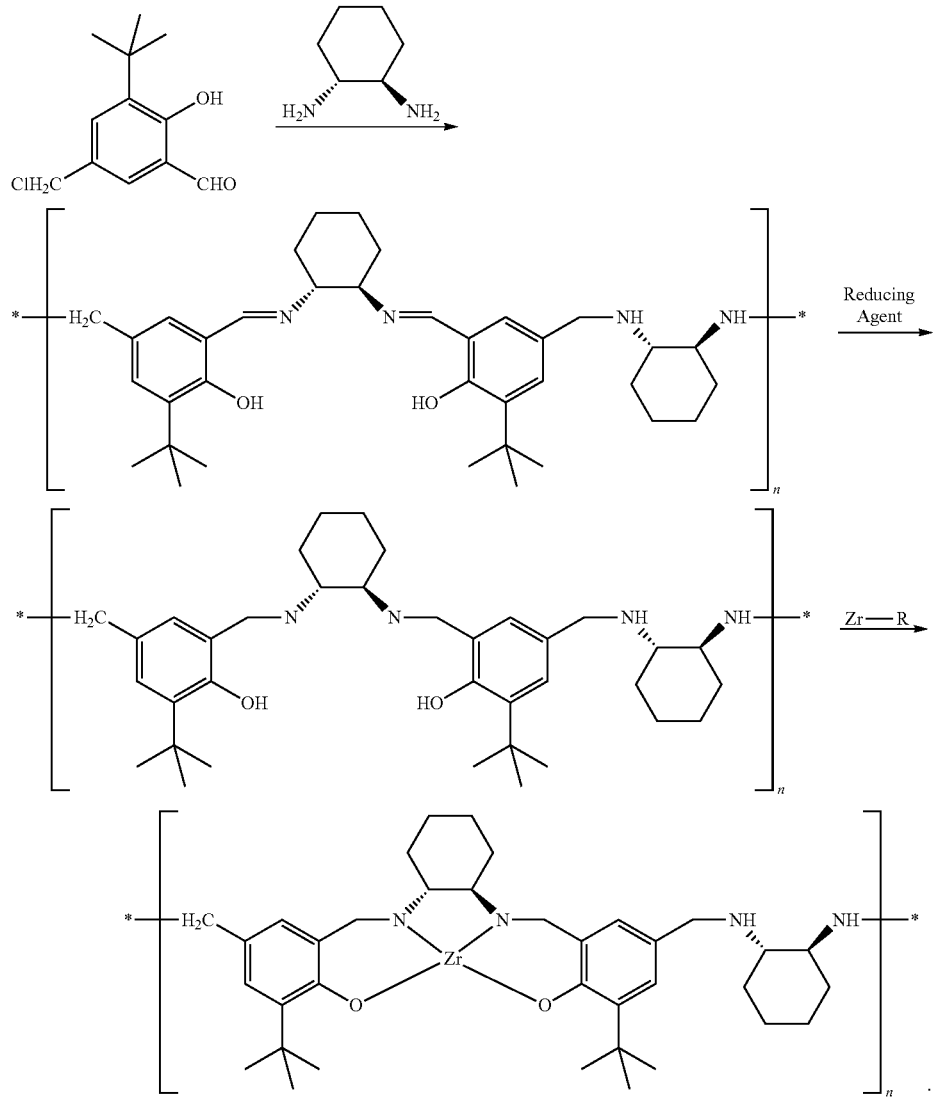

wherein n is a degree of polymerization and Zr—R is the zirconium compound.

2. The preparation method for S-indoxacarb according to claim 1, comprising the steps of:

adding tert-butyl hydroperoxide and 5-chloro-2-methoxycarbonyl-1-indanone ester to the polymerization catalyst solution obtained by the method of claim 1 to carry out asymmetric synthesis, wherein a mole ratio of 5-chloro-2-methoxycarbonyl-1-indanone ester:tert-butyl hydroperoxide:catalyst is 1:1.2-1.5:0.05-0.1; raising the temperature to 60-120° C. for reflux reaction for 4 hours, filtering the obtained mixture to recover polymer catalyst, the key intermediate 5-chloro-2-methoxycarbonyl-2-hydroxy-1-indanone is obtained by vacuum distillation of the filtrate, then, putting the recovered catalyst into toluene solvent to form suspension to continue to participate in the asymmetric synthesis reaction;

after obtaining the above-mentioned 5-chloro-2-methoxycarbonyl-2-hydroxy-1-indanone, making it react with carbobenzoxyhydrazide and diethoxymethane and finally, with hydrogenating deprotection, synthesizing S-indoxacarb with 4-trifluoromethoxy phenyl carbamate.

3. The preparation method for S-indoxacarb according to claim 1, wherein a mole ratio of 3-tert-butyl-5-(chloromethyl)salicylaldehyde to chiral cyclohexanediamine is 1:1-1.5, an amount of the solvent is 4-6 times of the mass of 3-tert-butyl-5-(chloromethyl)salicylaldehyde; the solvent is selected from the group consisting of methanol, ethanol, dichloromethane and dichloroethane.

4. The preparation method for S-indoxacarb according to claim 3, wherein the solvent is methanol.

5. The preparation method for S-indoxacarb according to claim 1, wherein the solvent in step (3) is selected from the group consisting of toluene, xylene, dichloroethane, n-hexane and tert butanol; and the reducing agent is selected from the group consisting of sodium borohydride, potassium borohydride and lithium aluminum hydride, and a mole ratio of the reducing agent used in step 3 to 3-tert-butyl-5-(chloromethyl)salicylaldehyde used in step 1 is 1-1.2:1.

6. The preparation method for S-indoxacarb according to claim 5, wherein the solvent in step (3) is toluene.

7. The preparation method for S-indoxacarb according to claim 1, wherein a mole ratio of the zirconium compound used in step 4 to 3-tert-butyl-5-(chloromethyl)salicylaldehyde used in step 1 is 1:1-2.

8. The preparation method for S-indoxacarb according to claim 7, wherein the zirconium compound in step (4) is zirconium(IV) acetylacetonate.

* * * * *